United States Patent
Coleman et al.

(10) Patent No.: US 7,554,090 B2
(45) Date of Patent: Jun. 30, 2009

(54) APPARATUS AND PROCESS FOR DOSE-GUIDED RADIOTHERAPY

(75) Inventors: C. Norman Coleman, Chevy Chase, MD (US); Robert Miller, Burtonsville, MD (US); Rosemary Altemus, Springfield, VA (US); Holly Ning, North Potomac, MD (US); Alan Lee Huston, Springfield, VA (US); Brian L. Justus, Springfield, VA (US); Paul Falkenstein, Alexandria, VA (US)

(73) Assignees: The United States of America as represented by the Department of Health and Human Services, Washington, DC (US); The United States of America as represent by the Secretary of the Navy, Washington, DC (US)

(*) Notice: Subject to any disclaimer, the term of this patent is extended or adjusted under 35 U.S.C. 154(b) by 0 days.

(21) Appl. No.: 10/548,391

(22) PCT Filed: Mar. 4, 2005

(86) PCT No.: PCT/US2004/006905

§ 371 (c)(1),
(2), (4) Date: Sep. 14, 2006

(87) PCT Pub. No.: WO2004/080522

PCT Pub. Date: Sep. 23, 2004

(65) Prior Publication Data

US 2007/0058778 A1 Mar. 15, 2007

Related U.S. Application Data

(60) Provisional application No. 60/453,934, filed on Mar. 11, 2003.

(51) Int. Cl.
*G01T 1/16* (2006.01)
(52) U.S. Cl. ............................................. 250/370.07
(58) Field of Classification Search ............. 250/370.07
See application file for complete search history.

(56) References Cited

U.S. PATENT DOCUMENTS

| | | | |
|---|---|---|---|
| 5,308,988 A * | 5/1994 | Siedband | 250/385.1 |
| 5,444,254 A * | 8/1995 | Thomson | 250/370.07 |
| 5,811,822 A | 9/1998 | Huston et al. | |
| 6,087,666 A | 7/2000 | Huston et al. | |
| 6,402,689 B1 * | 6/2002 | Scarantino et al. | 600/300 |
| 6,504,899 B2 | 1/2003 | Pugachev et al. | |
| 6,551,232 B1 | 4/2003 | Rivard | |
| 6,963,771 B2 * | 11/2005 | Scarantino et al. | 600/436 |
| 2001/0051766 A1 | 12/2001 | Gazdzinski | |
| 2002/0193685 A1 | 12/2002 | Mate et al. | |
| 2003/0125616 A1 * | 7/2003 | Black et al. | 600/407 |
| 2005/0020917 A1 * | 1/2005 | Scherch | 600/437 |
| 2005/0059879 A1 * | 3/2005 | Sutherland et al. | 600/411 |
| 2006/0017009 A1 * | 1/2006 | Rink et al. | 250/484.5 |
| 2006/0027756 A1 * | 2/2006 | Thomson et al. | 250/370.07 |

* cited by examiner

*Primary Examiner*—David P Porta
*Assistant Examiner*—Marcus H Taningco
(74) *Attorney, Agent, or Firm*—Townsend and Townsend and Crew LLP

(57) ABSTRACT

A method and an apparatus for dose-guided radiotherapy for a patient (P) having an identified radiotherapy target utilizes a radiation detecting array (R) of radiation-sensitive dosimeters for the real-time remote measurement of radiotherapy at the radiation detecting array (R). The radiation detecting array is positioned within the patient's (P) body along the treatment path before or after the identified radiotherapy target or the device may be positioned beyond the patient (P) to measure transit dose. A radiation source (A) for emitting radiation for radiotherapy along a treatment path through the patient (P) to the identified radiotherapy target is utilized. The method includes generating a predicted dose pattern of radiation at the placed radiation detecting array (R). The predicted dose pattern assumes an on-target radiation source (A) emitting the radiotherapy beam along the treatment path through the patient (P) to the identified radiotherapy target. Gating of the radiation source (A) can occur responsive to the comparing of the predicted dose pattern of radiation to the real-time dose pattern at the radiation detecting array (R). Radiation intensity can vary between low levels to a treatment level responsive to coincidence of the predicted dose pattern of radiation to the real-time dose pattern at the radiation detecting array (R).

28 Claims, 10 Drawing Sheets

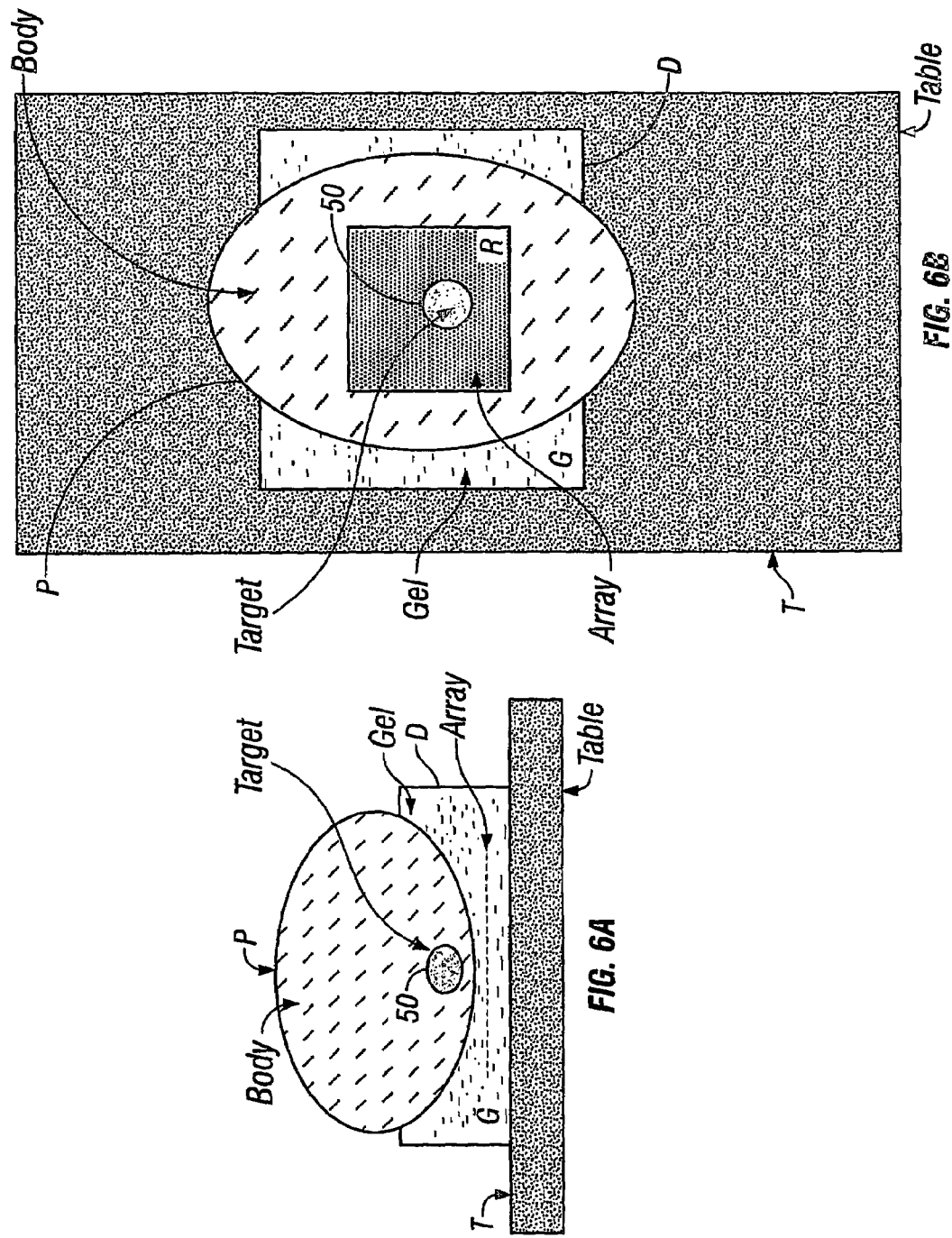

APPARATUS AND PROCESS FOR DOSE-GUIDED RADIOTHERAPY

CROSS-REFERENCES TO RELATED APPLICATIONS

This application claims priority from U.S. Provisional Patent Application Ser. No. 60/453,934 filed Mar. 11, 2003 entitled APPARATUS AND PROCESS FOR DOSE-GUIDED RADIOTHERAPY by the inventors herein.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

This invention relates to radiotherapy, such as the treatment of tumors in patients by radiation directed from linear accelerators or from radio active material (e.g. brachytherapy sources). More specifically, a grid of fiber optic radiation dosimeters detects in real-time the dose pattern of radiation administered. This real-time dose pattern is compared to a predicted dose pattern of targeted radiation being administered to a patient. Dosage is gated between a low radiation dose monitoring state and the prescribed radiation dose state responsive to coincidence of the predicted dose pattern to the real-time dose pattern. Radiation therapy with reduced margin and increased target dosage is enabled.

BACKGROUND OF THE INVENTION

In Huston et al. U.S. Pat. No. 6,087,666 entitled Optically Stimulated Luminescent Fiber Optic Radiation Dosimeter, an optically-stimulated luminescent radiation dosimeter system is disclosed. This system includes a radiation-sensitive optically-stimulated dosimeter which utilizes a doped glass material, disclosed in Huston et al. U.S. Pat. No. 5,811,822 entitled Optically Transparent, Optically Stimulable Glass Composites for Radiation Dosimetry, disposed at a remote location for storing energy from ionizing radiation when exposed thereto. The doped glass material releases the stored energy in the form of optically-stimulated luminescent light at a first wavelength when stimulated by exposure to light energy at a stimulating second wavelength. A fiber-optic waveguide communicates the released light to a photo detector at a remote location. Radiation dosage is measured in real-time at the remote location.

Radiotherapy approaches for treating humans and animals are known. Simply stated, oncologists irradiate tumors or "targets" to retard or eliminate the cancer. A brief review of the state-of-the-art treatment is warranted.

An oncologist in planning treatment physically examines a patient, looks at the patient's pathology, and observes previously generated patient images. Using all this information, the oncologist generates a treatment plan. This plan includes irradiating the tumor (hereafter target) at multistage intervals (for example, 36 discrete treatments or fractions) along a group of paths with the target at the point of path intersection. Since the radiation passes through healthy tissue on its way to and from diseased tissue, multiple paths for the administration of radiation are chosen. In that way, damage to healthy tissue is minimized and irradiation of the target maximized because of its location at the intersection of the group of paths.

Due to the nature of most cancers, it is required that the target receives the maximum prescribed dose of the oncologist's plan. Untreated tumor leads directly to recurrence of the cancer being treated. For this reason, typical treatment planning includes irradiating a volumetric "margin" around the target. Dependent upon target location, this volumetric margin can vary considerably. Some margin is needed due to uncertainty in knowing the precise boundary of the tumor. However, extra margin is applied due to patient and tissue/organ motion. Eliminating this extra margin can reduce the normal tissue toxicity and also allow for a higher dose to be administered to the tumor.

In the treatment planning process, the patient is placed in a treatment position and CT, MRI, PET and other images and scans are generated. The scans are fused to produce a three-dimensional digitized image of the patient in the treatment position. The target is identified in the three-dimensional digitized image of the patient. Thereafter, radiation treatment is delivered to the target through the patient in accordance with the oncologist's plan.

The oncologist typically predicts the total dosage delivered to the target utilizing known software in conjunction with his or her generated treatment plan. Dosage delivered at each discrete treatment can be the subject of a predicted irradiation pattern, usually at the target within the patient. In fact, the predicted irradiation pattern can be determined for any points within the three-dimensional digitized image obtained for the treatment plan.

For a recent disclosure illustrating the planning process, please see Pugachev et al. U.S. Pat. No. 6,504,899 issued Jan. 7, 2003.

This idealized description is not to be confused with reality. In general, when radiation therapy treatments are administered, the patient is immobilized and oriented to the treatment machine, lined up with external markers, and irradiated. Despite patient immobilization, internal organ motion can occur between treatments (so-called "inter-fraction" motion) and motion may occur during the treatment (so-called "intra-fraction" motion). To compensate for these motions and to assure that the target receives the prescribed radiation, the volumetric margin around the target is increased. Healthy tissue is irradiated along with the diseased tissue. Further, total dosage intensity at the target is decreased because of limitations of tolerance of the normal tissue which depends on both the dose of radiation and the volume of normal tissue irradiated.

Take for example where the target is in the lung. During breathing, portions of the lung move as much as 3 cm. Compounding the normal movement with patient anxiety during a radiation treatment, irradiating a target in the lung is a dynamic proposition. In the past, for full target irradiation, the margin of the radiation field has been increased considerably with resultant damage to healthy tissue. Similarly, extra rectal tissue is treated to account for prostate gland motion.

BRIEF SUMMARY OF THE INVENTION

A method of and apparatus for dose-guided radiotherapy for a patient having an identified radiotherapy target utilizes a radiation detecting array of radiation-sensitive dosimeters for the real-time remote measurement of radiotherapy at the radiation detecting array. The radiation detecting array is either placed within the patient along the treatment path before or after the identified radiotherapy target or exterior to the patient. A radiation source for emitting radiation along a treatment path through the patient to the identified radiotherapy target is utilized. The method includes generating a predicted dose pattern of radiation at the placed radiation detecting array. The predicted dose pattern assumes an on-target radiation source emitting the radiation along the treatment path through the patient to the identified radiotherapy target. When emitted radiation dosage occurs along the treatment path to the array, the predicted dose pattern of radiation is compared to the real-time dose pattern at the radiation detecting array to determine, in real-time, radiation coincidence to the identified radiotherapy target in the patient. The radiation detecting array can be placed adjacent to the identified radiotherapy target within the patient, or exterior to the patient. Gating of the radiation source can occur responsive to the comparing of the predicted dose pattern of radiation to the real-time dose pattern at the radiation detecting array. The radiation dose rate is controlled by varying the rate at which the radiation pulses are generated. After a patient is positioned for treatment according to the treatment plan, the patient is exposed to the beam for a short period of time, corresponding to a low or benign dose. This short exposure is sufficient to generate a dose image at the detector array. If the dose image corresponds to the predicted dose pattern, then the treatment continues in the manner prescribed by the oncologist. If the dose image does not correspond to the predicted dose pattern, then intervention is required to reposition the patient or the beam to obtain coincidence between the measured and predicted radiation patterns. The degree of coincidence between the measured dose image and the predicted dose pattern is monitored continuously during the treatment procedure. If at any time during the treatment, the measured dose image does not correspond to the predicted dose pattern, the treatment will be stopped and appropriate steps will be taken to reestablish proper coincidence. The radiation detecting array constitutes an improvement to the apparatus for radiotherapy. When combined with hardware that provides memory and image processing capabilities for comparing the predicted dose pattern to the real-time dose pattern at the array, a new apparatus for radiotherapy is disclosed.

BRIEF DESCRIPTION OF THE DRAWINGS

FIG. 6A is a schematic section taken through the body of a patient resting on a pad of tissue equivalent gel with an array disposed within the tissue equivalent gel; and, FIG. 6B is a schematic plan of FIG. 6A.

DETAILED DESCRIPTION OF THE INVENTION

Figure 1A:
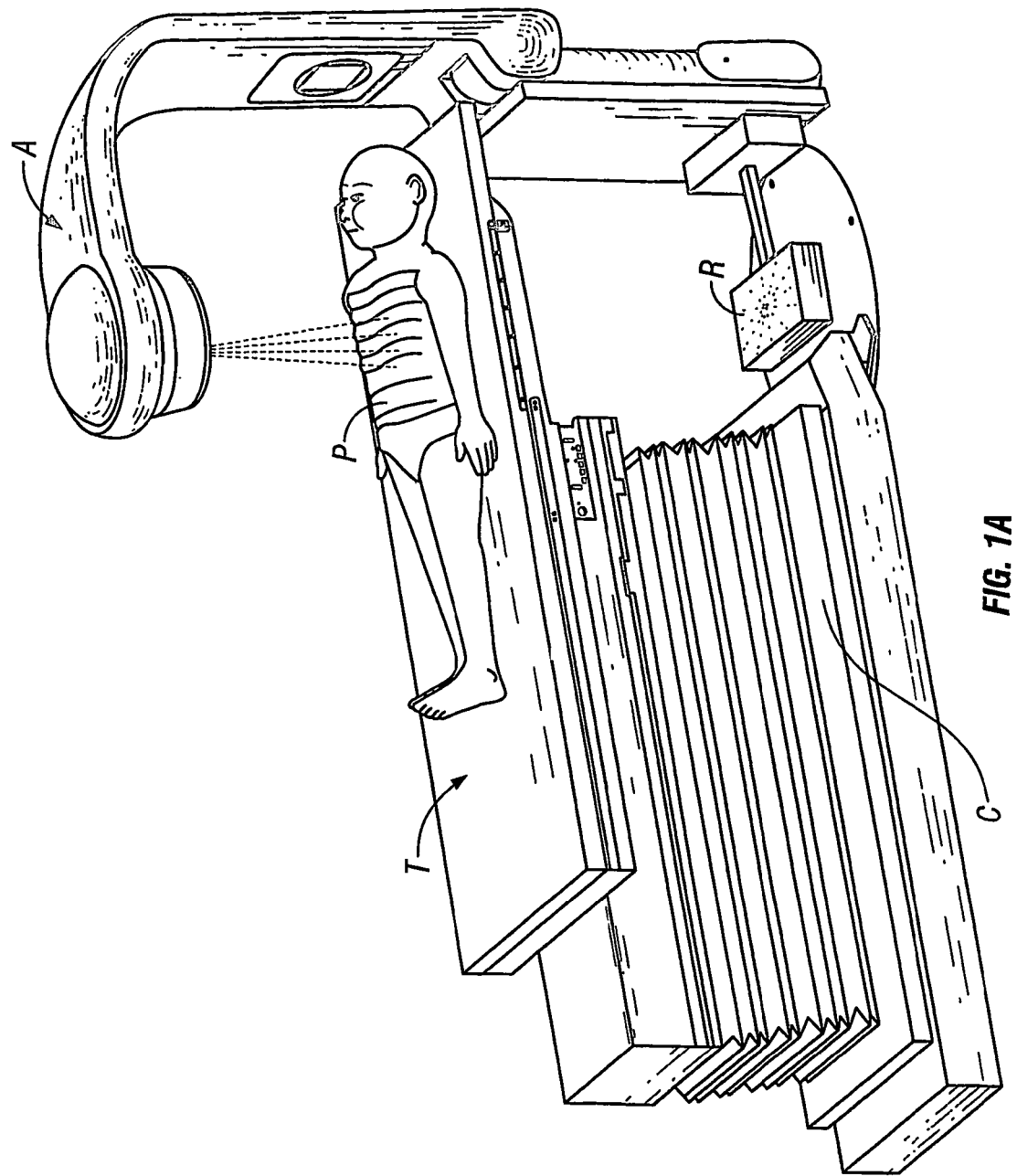
FIG. 1A is a perspective view of a patient on a supporting table underlying a linear accelerator schematically illustrating radiation treatment to the lung with a dose meter array located exterior of the patient and below the table supporting the patient.

Referring to FIG. 1A, a patient P is shown positioned on table T underlying accelerator A. A real-time dosimeter array R is shown schematically positioned below table T. As will hereinafter become more apparent, array R can be positioned either interior of the patient, as for example in an inserted catheter at or near the identified radiotherapy target, or positioned at the exterior of the patient along the treatment path from the radiotherapy target, as for example being positioned coincident to the table surface after the radiation has passed through the patient. Computer C is illustrated below table T; it will be realized that the location of the computer is completely discretionary.

The accelerator A operates by generating short (~5-microsecond) pulses of radiation. The overall quantity of radiation administered to the patent is determined by the total number of pulses that the patient receives. As will be made clear, the dosage rate changes from a few pulses per unit time where the patient is out of position to a prescribed treatment level where the patient is in position.

In the preferred embodiment here, we use a linear accelerator A. It will be understood that other radiation sources will operate as well. For example, one can use this on radiation sources other than linear accelerators, including radioactive sources such as cobalt 60, iridium, iodine, palladium, and particle beams including protons, electrons and neutrons.

Figure 1B:
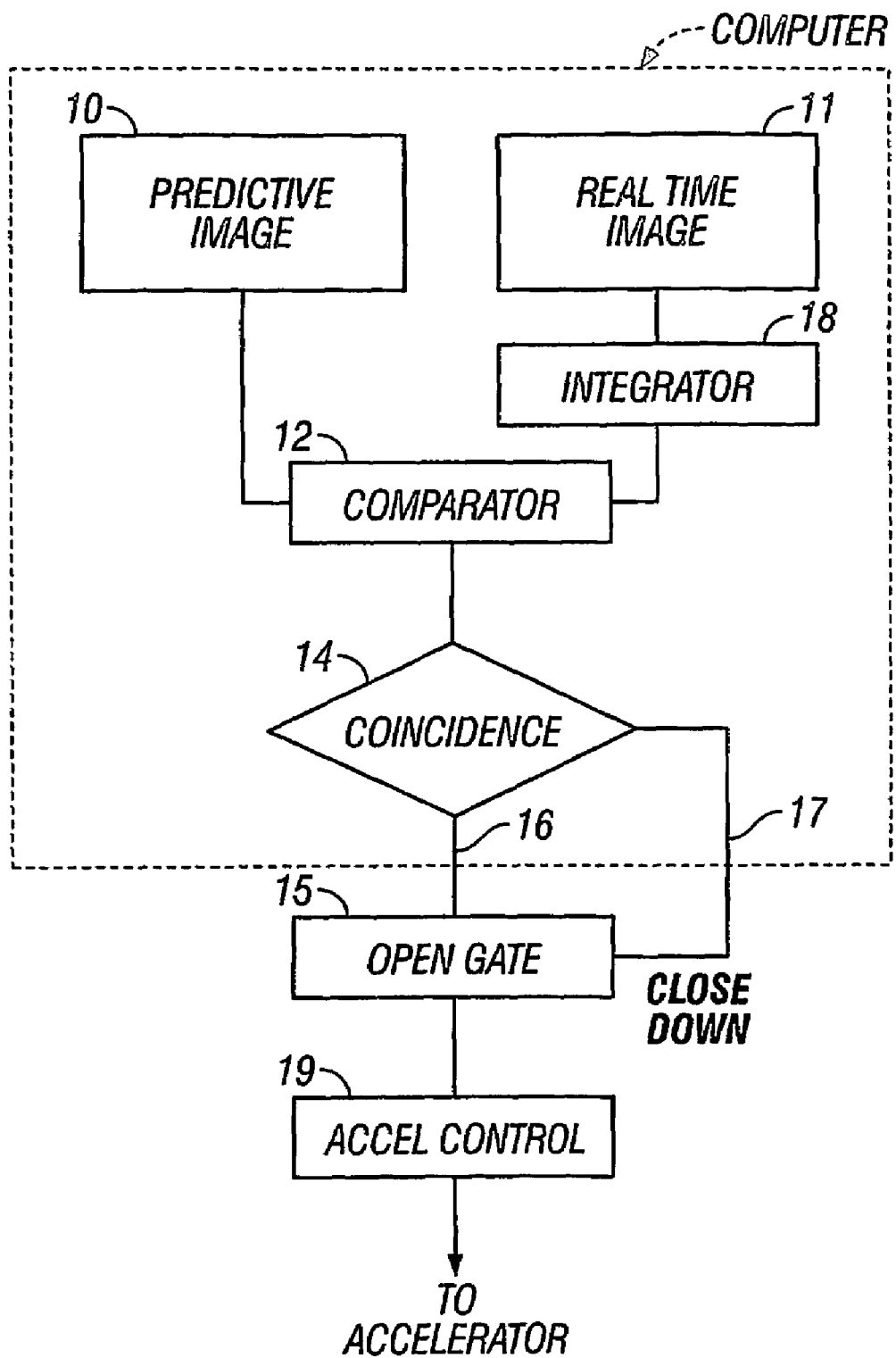
FIG. 1B is a block diagram illustrating the controlling computer logic including comparing the predicted image with a real-time image to gate the linear accelerator for patient treatment.

Referring to FIG. 1B, a block diagram illustrating gating of the accelerator A is shown. Specifically, a predicted image 10 is input to the computer. The predicted image 10 is conventionally generated by merging area scans. Specifically, patient P is placed in the treatment position. Thereafter, the patient is subject to a number of scans. The scans can include magnetic resonance imaging (MRI), computer-generated tomographic scans (CT), and the like. Once these discrete scans are generated, they are conventionally merged to produce the predicted images. Such conventionally produced predicted images are illustrated with respect to FIGS. 4A, 4B, 5A, and 5B.

Real-time image 11 is generated from array R. Referring to Huston et al. U.S. Pat. No. 6,087,666 issued Jul. 11, 2000 entitled "Optically Stimulated Luminescent Fiber Optic Radiation Dosimeter", a dosimeter having broad dynamic range is disclosed for radiation having ionizing effect on the disclosed dosimeters. Simply stated, over a dose range including approximately six orders of magnitude, the disclosed dosimeter can report, in real-time, the radiation received.

The dosimeter array R can vary from that disclosed in Huston et al. U.S. Pat. No. 6,087,666. By way of example, scintillating optical fibers or electronic detector arrays can be used. Further, and where the array is placed along the treatment path from the radiotherapy target to the exterior of the patient, it will be understood that the term "radiation detecting array" includes electronic portal imaging technologies. In short, any array which is capable of producing from the treatment radiation source a real-time image of, at, or adjacent to, the radiotherapy target or along the treatment path from the radiotherapy target exterior to the patient will suffice.

Some general comment can be made about the real-time image 11 necessary for the practice of this invention.

We propose utilizing the detector of Huston et al. U.S. Pat. No. 6,087,666 configured in a remotely monitored array R. By monitoring a plurality of points in an array (preferably at least 8 such detectors), a real-time dosimeter image produced by accelerator A can be utilized to control patient treatment. Further, accelerators have the capability of being gated as to the dose delivered per unit time. In the preferred embodiment disclosed hereinafter, we utilize the accelerator A gated to a low level per unit time to produce at the array R a monitoring real-time image. Thereafter, utilizing this monitoring real-time image, we compare the monitored array points to the predicted image 10. Upon seeing coincidence between the predicted image 10 and the real-time image 11, gating of the accelerator to prescribed treatment intensity per unit of time occurs.

It will be understood that the contrast level of the real-time image array 11 can be altered so that during full intensity treatment the real-time dose being administered to the patient produces a real-time image which can be compared to the predicted image. If during the full intensity treatment the target moves, gating of the accelerator to the low radiation level per unit of time can occur.

Predicted image 10 will in the normal case be quite complete. For example, by merging soft tissue discriminatory scans such as MRI scans with bone density discriminatory scans such as CT scans, images such as those generated in FIGS. 4B and 5B can be routinely generated. This is to be contrasted with real-time image 11. In the case of the real-time image 11, it is only necessary to sample the image produced by the linear accelerator A. For example, and taking the schematic layout of the internal dosimeter probe illustrated in FIG. 3A, it will be seen that only 8 sample points are included for the real-time image 11. With 8 such points, coincidence or non coincidence between predicted image 10 and real-time image 11 can be determined. It should be noted that sampling a larger number of points will result in greater precision.

Returning to schematic FIG. 1B, predicted image 10 and real-time image 11 are analyzed for coincidence at comparator 12. When coincidence is determined, coincidence gate 14 emits a signal 16 to accelerator gate 15 to fully open accelerator control 19 causing accelerator A to emit through accelerator control 19 a treating beam of the prescribed dosage per unit of time. Alternatively, when coincidence is not determined, coincidence gate 14 emits a signal 17 closing down gate 15. The accelerator control 19 emits a signal to accelerator A causing radiation to be emitted at the low level.

Figure 3A:
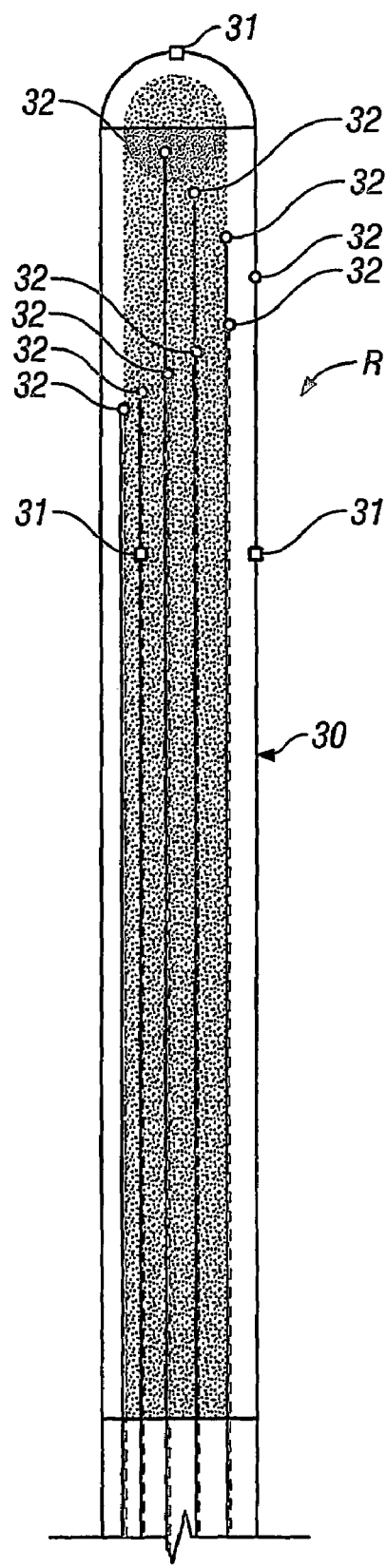
FIG. 3A is a schematic layout of an internal dosimeter probe array showing a detector array together with fiducial markers.
Figure 3B:
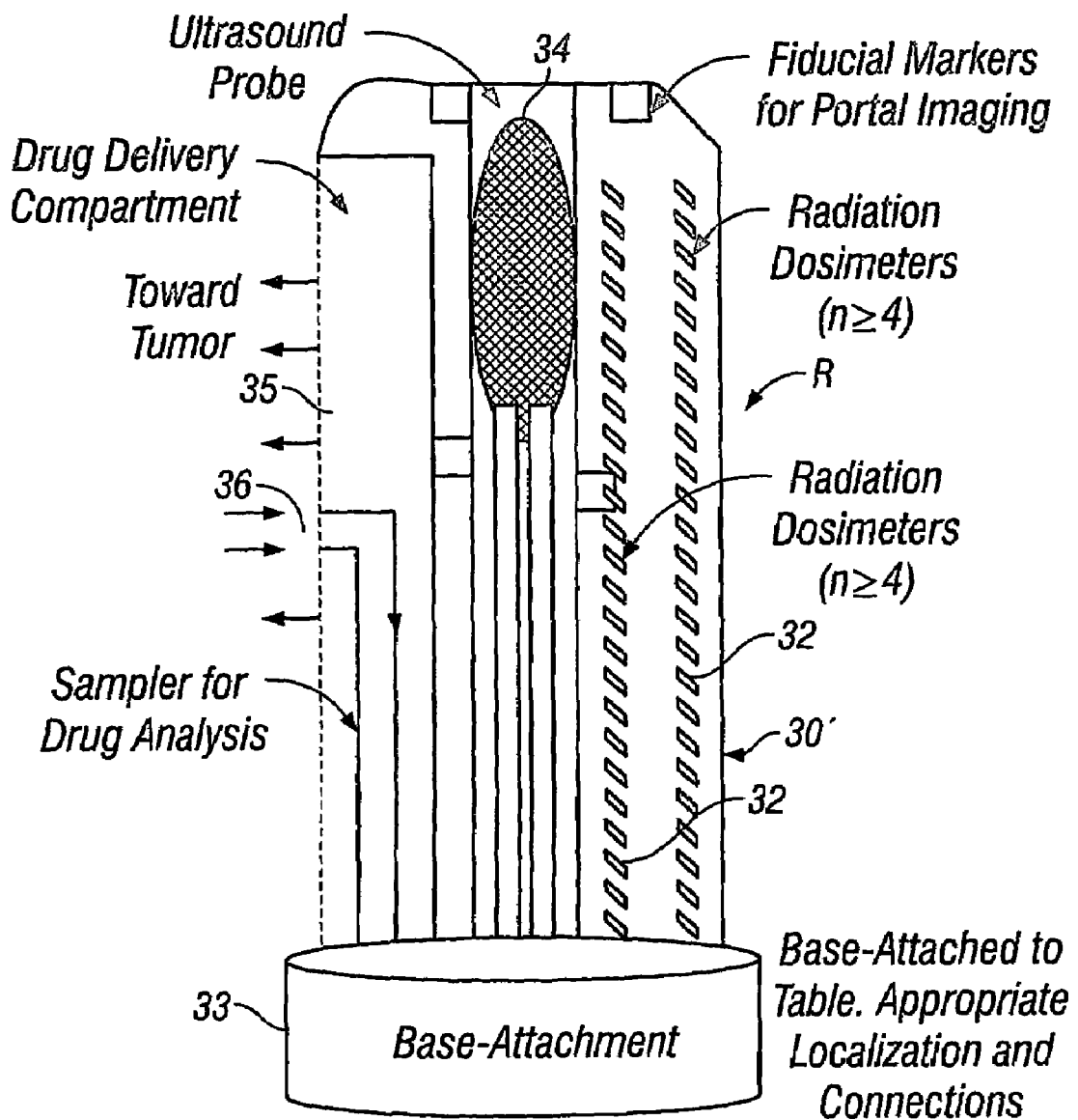
FIG. 3B is a schematic layout of an internal dosimeter probe array in conjunction with a catheter having ancillary apparatus for use in conjunction with the dosimeter probe array.
Figure 4A:
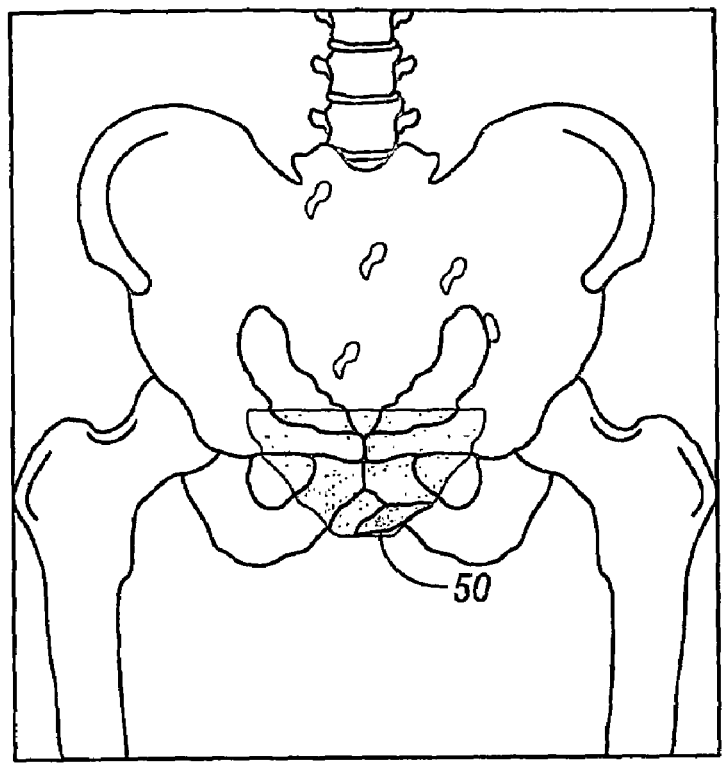
FIG. 4A is a predicted image of a patient having prostate cancer illustrating the cancer located in the pelvic area with the cancer target identified.
Figure 4B:
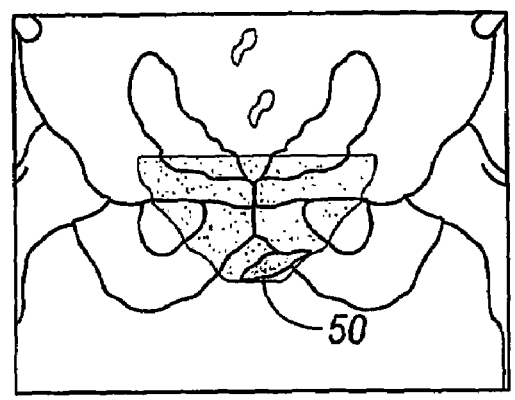
FIG. 4B is a predicted image in the vicinity of the prostate illustrating the target on an expanded basis.

Referring to FIGS. 3A and 3B, two varieties of the arrays utilized with this invention are illustrated. Referring to FIG. 3A, an array R positioned with respect to catheter 30 is illustrated. The array R is of the type that is best utilized for insertion to the patient P being treated. For example, it can be used as a rectal probe during treatment of prostate cancer, as illustrated in FIGS. 4A and 4B hereinafter. Catheter 30 includes fiducials 31 which can measure the colon center line invasion of the catheter to a site proximate to the prostate cancer being treated. Fiducials 31 not only determine the proximity of the catheter 30 to the treated prostate but additionally can be used to orient the array with respect to the radiation beam after the catheter is being administered to the patient. Further, catheter 30 includes remote fiber monitors 32 constructed in accordance with Huston et al., U.S. Pat. No. 6,087,666. These remote fiber monitors 32 and fiducials 31 are typically disposed on a cylindrical structure with the dosimeter probes 32 and the fiducial markings arranged around the periphery. As such, the probes and fiducials are arranged in a three-dimensional arrangement. Once positioned, the rectal probe stabilizes the position of the prostate gland, preventing it from moving during the course of the therapy session.

Once the catheter of FIG. 3A is inserted adjacent to and oriented with respect to the target being treated (for example of prostate illustrated in FIG. 4), accelerator A is typically gated to a low level. At this low level, the beam from accelerator A can produce high contrast image points at each of the remote fiber monitors 32. Presuming a high contrast image of the prostate sections that are illustrated in FIG. 4B, the discrete sample points of the remote fiber monitors 32 will sample the real-time image 11 relative to the predicted image 10. Where coincidence is present, accelerator A will be gated to full treatment level.

Referring to FIG. 3B, catheter (or probe) 30' is illustrated in more detail. The remote fiber monitors 32, numbering in excess of four such monitors, are shown disposed from a base 33. These monitors 32 are typically disposed in a three dimensional array within catheter 30'. Ultrasound probe 34 is shown disposed within catheter 30' to enable ultrasound imaging to assist catheter positioning. Catheter 30' includes an inflatable cuff that holds the catheter firmly in place and stabilizes the position of the target (for example, the prostate gland illustrated in FIG. 4) during the course of the radiotherapy session. Further, drug delivery compartment 35 and drug delivery sampler 36 are illustrated. Typically compartment 35 and sampler 36 enable radiation mitigating drugs to be administered to the patient P. For example, where catheter 30' is inserted rectally to be proximate to cancer of the prostate, it is desirable that the radiation have minimal effect on the tissue of the rectum. By emitting drugs from compartment 35 and monitoring drug density through drug delivery sampler 36, the optimum presence of the radiation mitigating drugs can be maintained throughout the desired treatment.

Referring to FIG. 1A, the reader will understand that it is not necessary to place array R within patient P. Specifically, array R is shown below to the top of table T.

The reader will understand that there are any number of prior art programs that can predict at selected planes through out the patient the amount of radiation emitted along any discrete path to a target within the patient. These very same programs can be adapted by those having skill in the art to planes taken exterior of the patient. Thus, in FIG. 1A, an array of the remote fiber monitors 32 is shown below the top of table T. Regarding such arrays, they can be placed on planes exterior of the patient which are typically normal to the beam of radiation from accelerator A. Referring back to FIG. 1A, the array R there illustrated is shown below the level of table T. Alternately, arrays R can be co-incident to the top of table T. Further, the array could just as well be a freestanding plane aligned with respect to both the patient, table and accelerator but exterior of the patient. For example, where the beam from accelerator A is angularly inclined with respect to the table T, an array R could be placed on the table canted to an angle so as to be normal to the beam of radiation from the accelerator.

Figure 2:
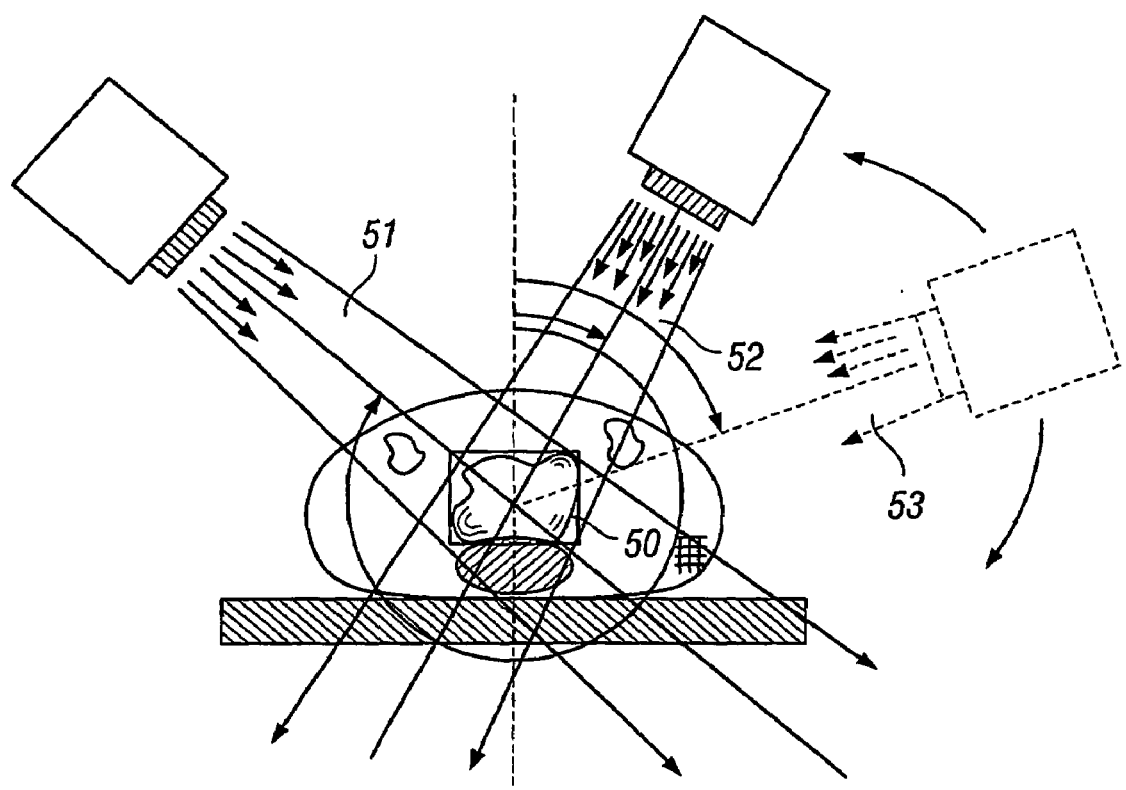
FIG. 2 is a schematic view of the patient illustrating a treatment plan having three discrete angles for radiation treatment to a target located within the patient.

Referring to FIG. 2, it will be understood the patient P having a cancer target 50 will be treated by radiation from the accelerator A from a number of different angles. All treatment paths will typically be coincident to the cancer target 50. At the same time, the treatment paths will have differing entrance and exit paths. This will be done to minimize radiation to healthy tissue and to concentrate radiation on diseased tissue.

In the description that follows, for simplicity we only track radiation incident to a patient along a single path. Typically, and for treatment along multiple paths, differing paths of incidence of radiation to the target 50 on the patient will be utilized. For example, in FIG. 2, discrete radiation paths 51, 52 and 53 all having differing angular inclination with respect to the patient are shown.

Referring to FIG. 4A, an image of the pelvic region of a patient having prostate cancer is illustrated. Referring to FIG. 4B, the area immediate to the diseased prostate is shown in an expanded view. This area shows cancer target 50 outlined with respect to the prostate. Unfortunately, prostates are notorious for movement. First, patient nervousness can cause muscular flexure in the vicinity of the pelvis. Pelvic movement with resultant prostate movement results. Moreover, gas in the rectum can effect overall prostate movement. Furthermore, the patient (especially during initial treatment) can himself dynamically (and nervously) move. Simply stated, the prostate is a dynamic target during radiation treatment.

Figure 4C:
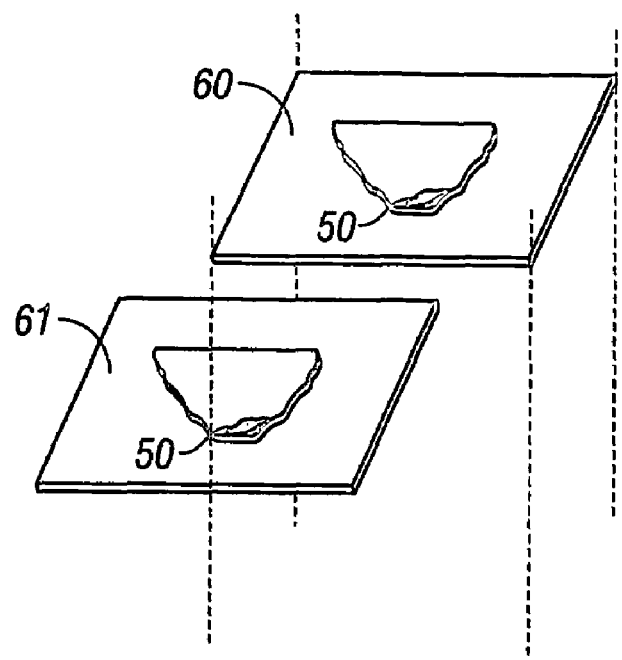
FIG. 4C is a perspective view of non coincidence between the predicted image and the real-time dosimeter image of the prostate resulting in gating of the accelerator to a low radiation monitoring level.

Referring to FIG. 4C, an oversimplified view of non coincidence between predicted prostate image 60 and real-time prostate image 61 is illustrated. The images are shown to be exactly the same but displaced with respect to the collimated radiation emitted from accelerator A. In actual fact, and assuming local organ intra-fraction or inter-fraction movement, non coincidence of the images will not be as simple. Specifically, the content of predicted prostate image 60 and real-time prostate image 61 will be two discreetly different images, much as two pictures of the same human face with two different expressions will be discreetly different images. Presuming that array R samples real-time prostate image 61, coincidence to predicted prostate image 60 will not occur. Accordingly, accelerator A will be gated to emit a low level of radiation.

Figure 4D:
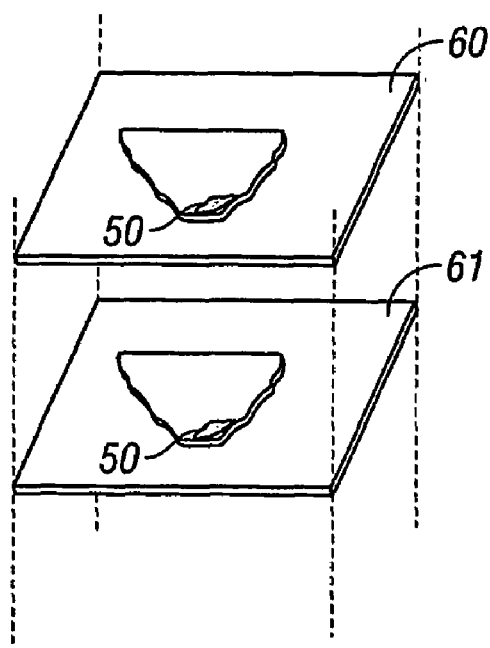
FIG. 4D is a perspective view of coincidence between the predicted image and the real-time dosimeter image of the prostate resulting in gating of the accelerator to a prescribed treatment level.

Referring to FIG. 4D, a view of coincidence between predicted prostate image 60 and real-time prostate image 61 is illustrated. The images are shown to be exactly the same and registered with one another with respect to the collimated radiation emitted from accelerator A. Presuming that array R samples real-time prostate image 61 coincident to predicted prostate image 60 will occur. Accordingly, accelerator A will be gated to emit a full intensity treatment of radiation.

Figure 5A:
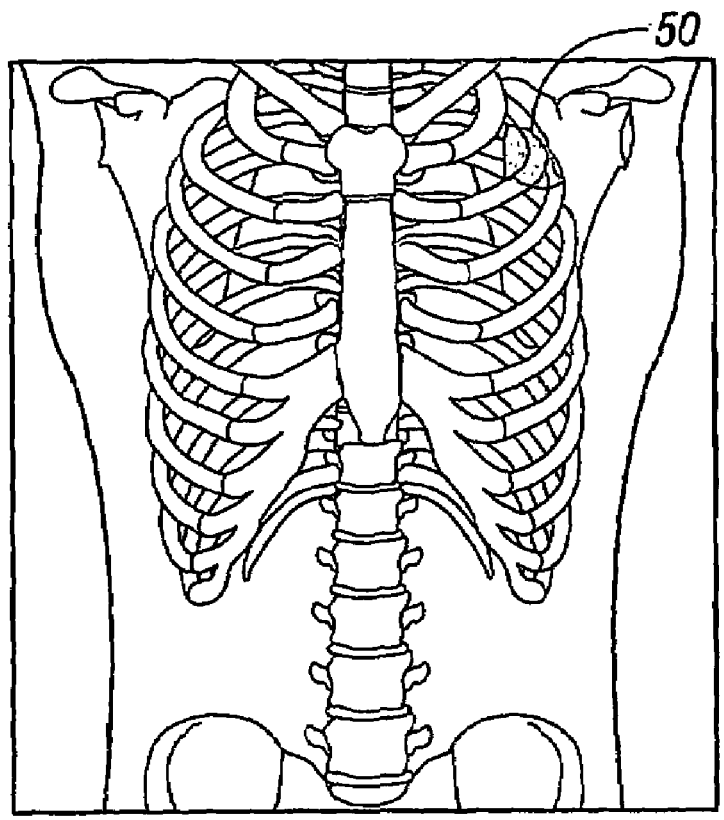
FIG. 5A is a predicted image of a patient having lung cancer illustrating the cancer located in the chest area with the target identified.

Referring to FIG. 5A, an image of the patient having lung cancer is illustrated in the vicinity of the chest and rib cage. Presuming that the cancer target 50 is on a surface of the lung, a target having unusual dynamic excursion is illustrated. First, it is normal for the patient to shallowly breathe; such shallow breath causes cancer target 50 excursion. Second, it is interesting to consider the case of normal human breathing. Such normal breathing includes periods of shallow breath followed by intermittent deeper breaths. The intermittent deeper breaths are random, unpredictable, and especially prevalent where the patient is in any kind of this situation causing nervous unease (such as initial radiation treatments for cancer to the chest). Finally, overall patient movement on the table can likewise contribute to cancer target 50 misalignment.

Figure 5B:
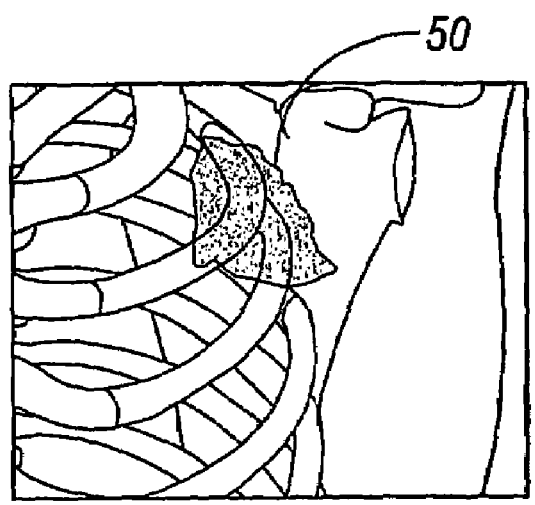
FIG. 5B is an predicted image in the vicinity of the lung illustrating the target on an expanded basis.

Referring to FIG. 5B, the area immediate to the diseased lung is shown in an expanded view. This area shows cancer target 50 outlined with respect to the portion of the lung shown.

Figure 5C:
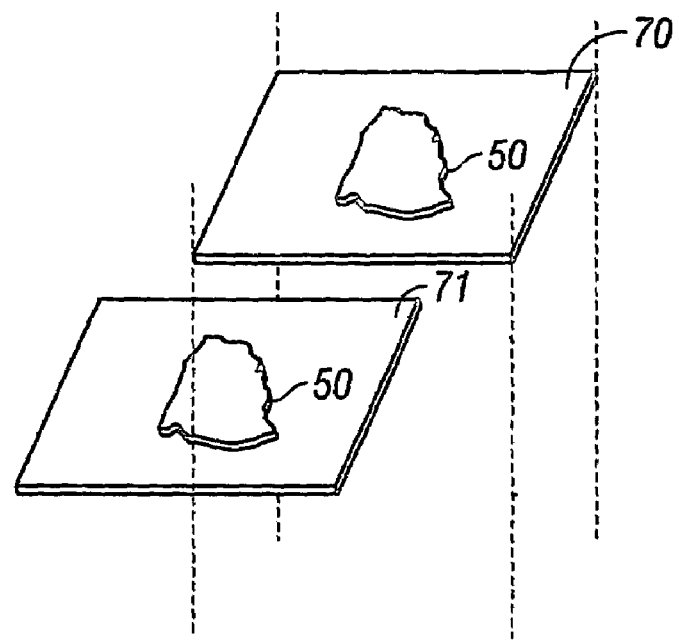
FIG. 5C is a perspective view of non coincidence between the predicted image and the real-time dosimeter image of the lung resulting in the gating of the accelerator to a low radiation monitoring level.

Referring to FIG. 5C, an oversimplified view of non coincidence between predicted lung image 70 and real-time with lung image 71 is illustrated. Again the images are shown to be exactly the same but displaced with respect to the collimated radiation emitted from accelerator A. Again non-coincidence of the images will not be as simple. Accordingly, accelerator A will be gated to emit a low level of radiation.

Figure 5D:
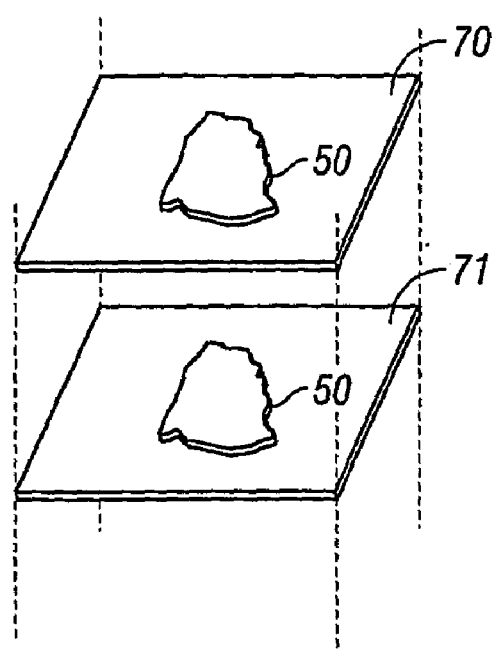
FIG. 5D is a perspective view of coincidence between the predicted image and the real-time dosimeter image of the lung resulting in the gating of the accelerator to a full treatment level.

Referring to FIG. 5D, a view of coincidence between the predicted lung image 70 and real-time lung image 71 is illustrated. The images are shown to be exactly the same and registered to one another with respect to the collimated radiation emitted from the accelerator A. Presuming that array R samples real-time lung image 71, coincidence to predicted lung image 70 will occur. Accordingly, accelerator A will be gated to emit a full intensity treatment of radiation.

Referring to FIGS. 6A and 6B, pad D containing tissue equivalent gel G is shown disposed on table T. An array R is contained within the gel G. Pad D and gel G conforms to the patient's body so that there is no air gap between the body and the detector array. The MRI and CT scans are performed with the gel/detector array in position so that current treatment planning systems can be utilized to determine the dose distribution at the position of the array. Utilizing this apparatus, array R placed outside the body can be utilized without determining dose distribution leaving the skin of the patient and proceeding through atmosphere.

It will be understood that other expedience could as well be used. For example, array R could be contained within conformable pad which is wrapped tightly to the patient's skin.

What is claimed is:

1. A method of dose-guided radiotherapy for a patient having an identified radiotherapy target, which radiotherapy is administered in a plurality of doses within a single session, comprising the steps of:

providing a radiation detecting array of radiation-sensitive detectors for the remote measurement of real-time dose pattern at the radiation detecting array;

providing a radiation source for emitting radiation along a treatment path through the patient to the identified radiotherapy target;

placing the radiation detecting array (a) within the patient along the treatment path before or after the identified radiotherapy target or (b) exterior to the patient's body on the treatment path;

generating a predicted dose pattern of radiation at the placed radiation detecting array;

emitting radiation along the treatment path through the patient's body to the array to receive the real-time dose pattern;

comparing the predicted dose pattern of radiation to the real-time dose pattern at the radiation detecting array during said session to determine coincidence of radiation with the identified radiotherapy target in the patient, and gating the radiation source responsive to the comparing of the predicted dose pattern of radiation to the real-time dose pattern at the radiation detecting array.

2. The method of dose-guided radiotherapy for a patient having an identified radiotherapy target according to claim 1 and wherein:
said placing of the radiation detecting array is adjacent to the identified radiotherapy target within the patient.

3. The method of dose-guided radiotherapy for a patient having an identified radiotherapy target according to claim 1 and wherein:
said placing of the radiation detecting array is exterior of the patient.

4. The method of dose-guided radiotherapy for a patient having an identified radiotherapy target according to claim 1, wherein the gating step comprises:
gating the radiation source to a treatment level responsive to coincidence of the predicted dose pattern of radiation to the real-time dose pattern at the radiation detecting array.

5. The method of dose-guided radiotherapy for a patient having an identified radiotherapy target according to claim 1, wherein the gating step comprises:
gating the radiation source to a low level per unit of time responsive to non-coincidence of the predicted dose pattern of radiation to the real-time dose pattern at the radiation detecting array.

6. The method of dose-guided radiotherapy for a patient having an identified radiotherapy target according to claim 5, wherein the gating step comprises:
utilizing the real-time dose pattern produced by the radiation source at the low level per unit of time to move the patient and accelerator into a position of coincidence between the predicted dose pattern and the real-time dose pattern measured at the array.

7. The method of dose-guided radiotherapy for a patient having an identified radiotherapy target according to claim 1, wherein the gating step comprises:
moving the provided radiation source and patient relative to one another responsive to the comparing of the predicted dose pattern of radiation to the real-time dose pattern at the radiation detecting array to produce coincidence of the predicted dose pattern to the real-time dose pattern at the detecting array.

8. The method of dose-guided radiotherapy for a patient having an identified radiotherapy target according to claim 1, wherein the step of placing the radiation detecting array exterior to the patient's body on the treatment path includes:
providing a pad with tissue equivalent gel, which pad has disposed in said gel said radiation detecting array; and,
contacting pad with the patient to enable the pad with tissue equivalent gel to constitute a continuum of the patient's body.

9. The method of dose-guided radiotherapy for a patient having an identified radiotherapy target according to claim 1, wherein:
the detector array is positioned in the patient's rectum adjacent to the prostate gland.

10. The method of dose-guided radiotherapy for a patient having an identified radiotherapy target according to claim 9, wherein:
the detector array is disposed in an inflatable rectal probe that stabilizes the position of the prostate gland and prevents the prostate gland from moving during the radiotherapy procedure.

11. The method of dose-guided radiotherapy for a patient having an identified radiotherapy target according to claim 9, wherein:
the rectal probe contains an ultrasound probe to position the detector array with respect to the prostate gland.

12. The method of dose-guided radiotherapy for a patient having an identified radiotherapy target according to claim 9, wherein:
the rectal probe includes a drug delivery compartment to supply radiation mitigating drugs.

13. The method of dose-guided radiotherapy for a patient having an identified radiotherapy target according to claim 9, wherein:
the rectal probe includes a drug delivery sampling port to monitor drug density during the radiotherapy procedure.

14. The method of dose-guided radiotherapy for a patient having an identified radiotherapy target according to claim 9, wherein:
the detector array is disposed in a rectal probe that stabilizes the position of the prostate gland and prevents the prostate gland from moving during the radiotherapy procedure, which probe has an inflatable cuff.

15. The method of dose-guided radiotherapy for a patient having an identified radiotherapy target according to claim 14, further wherein said rectal probe has a first end and a second end and said inflatable cuff is positioned closer to said first end than to second end.

16. The method of dose-guided radiotherapy for a patient having an identified radiotherapy target according to claim 1, further wherein said radiotherapy source is a linear accelerator.

17. In the combination of,
a patient having an identified radiotherapy target; and,
a radiation source for emitting radiation along a treatment path through the patient to an identified radiotherapy target; the improvement comprising:
a detecting array of radiation-sensitive dosimeters for the real-time dose measurement of radiation within the patient along the treatment path before or after the identified radiotherapy target or exterior to the patient's body on the treatment path,
a memory for retaining a predicted dose pattern of the radiation source at the detecting array; and,
means for detecting coincidence between the predicted dose pattern and the real-time dose pattern to enable alignment of the radiation source with respect to a patient.

18. The combination of claim 17, wherein: the detecting array is placed outside of the patient.

19. The combination of claim 18 and wherein:
the detecting array is disposed within a gel; and,
the gel is confined within a pad for direct contact with the patient.

20. The combination of claim 17, wherein:
the detecting array is placed inside of the patient.

21. A method of dose-guided radiotherapy for a patient having an identified radiotherapy target comprising the steps of:
providing a radiation detecting array of radiation-sensitive detectors for the remote measurement of real-time dose pattern at the radiation detecting array;
providing a radiation source for emitting radiation along a treatment path through the patient to the identified radiotherapy target;
placing the radiation detecting array (a) within the patient along the treatment path before or after the identified radiotherapy target or (b) exterior to the patient's body on the treatment path;
generating a predicted dose pattern of radiation at the placed radiation detecting array;

emitting radiation along the treatment path through the patient's body to the array to receive the real-time dose pattern;

comparing the predicted dose pattern of radiation to the real-time dose pattern at the radiation detecting array to determine coincidence of radiation with the identified radiotherapy target in the patient, and gating the radiation source responsive to the comparing of the predicted dose pattern of radiation to the real-time dose pattern at the radiation detecting array.

22. The method of dose-guided radiotherapy for a patient having an identified radiotherapy target according to claim 21, and:

placing the radiation detecting array adjacent to the identified radiotherapy target within the patient.

23. The method of dose-guided radiotherapy for a patient having an identified radiotherapy target according to claim 21, and:

placing the radiation detecting array exterior of the patient.

24. The method of dose-guided radiotherapy for a patient having an identified radiotherapy target according to claim 21, wherein said gating of said radiation source is to a low level per unit of time when there is non-coincidence of the predicted dose pattern of radiation to the real-time dose pattern at the radiation detecting array.

25. The method of dose-guided radiotherapy for a patient having an identified radiotherapy target according to claim 21, wherein said gating of said radiation source is to a high level per unit of time when there is coincidence of the predicted dose pattern of radiation to the real-time dose pattern at the radiation detecting array.

26. The method of dose-guided radiotherapy for a patient having an identified radiotherapy target according to claim 21, further comprising:

moving the provided radiation source and patient relative to one another responsive to the comparing of the predicted dose pattern of radiation to the real-time dose pattern at the radiation detecting array to produce coincidence of the predicted dose pattern to the real-time dose pattern at the detecting array.

27. The method of dose-guided radiotherapy for a patient having an identified radiotherapy target according to claim 21, further wherein:

said radiation source is a linear accelerator.

28. A method of dose-guided radiotherapy for a patient having an identified radiotherapy target comprising the steps of:

providing a radiation detecting array of radiation-sensitive detectors disposed within a tissue equivalent gel for the remote measurement of real-time dose at the radiation sensitive detectors;

providing a radiation source for emitting radiation along a treatment path through the patient to the identified radiotherapy target;

contacting the patient with the radiation detecting array;

generating a predicted dose pattern of radiation at the radiation detecting array;

emitting radiation along the treatment path through the patient's body to the radiation detecting array to receive the real-time dose pattern; and comparing the predicted dose pattern of radiation to the real-time dose pattern at the radiation detecting array to determine coincidence of radiation with the identified radiotherapy target in the patient, and gating the radiation source responsive to the comparing of the predicted dose pattern of radiation to the real-time dose pattern at the radiation detecting array.

* * * * *